United States Patent [19]

Steiner et al.

[11] 4,263,157
[45] Apr. 21, 1981

[54] CHLORINATED DERIVATIVES OF BUTYRIC ACID AS USEFUL LUBRICANT ADDITIVES AND LUBRICANTS CONTAINING SAME

[75] Inventors: Eginhard Steiner, Füllinsdorf; Andreas Schmidt, Reinach, both of Switzerland

[73] Assignee: Ciba-Geigy Corporation, Ardsley, N.Y.

[21] Appl. No.: 31,281

[22] Filed: Apr. 18, 1979

[30] Foreign Application Priority Data

Apr. 26, 1978 [CH] Switzerland .......................... 4504/78

[51] Int. Cl.$^3$ .............................................. C10M 1/30
[52] U.S. Cl. ................................. 252/54.6; 252/33.6; 252/34; 252/51.5 A; 560/130; 560/192; 560/226; 560/226; 560/230; 562/602; 564/209
[58] Field of Search ................... 252/33.6, 34, 51.5 A, 252/54.6; 560/130, 192, 226, 230; 562/602; 260/561 HL

[56] References Cited

U.S. PATENT DOCUMENTS

| | | | |
|---|---|---|---|
| 2,262,773 | 11/1941 | Lincoln et al. | 252/54.6 X |
| 2,680,717 | 6/1954 | Little, Jr. | 252/34 X |
| 2,715,107 | 8/1955 | Talley et al. | 252/54.6 X |
| 2,812,307 | 11/1957 | Saives | 252/54.6 X |
| 3,117,932 | 1/1964 | Péras | 252/54.6 |
| 3,269,948 | 8/1966 | Furey | 252/34 |
| 3,284,355 | 11/1966 | Papayannopolus | 252/54.6 X |
| 3,565,926 | 2/1971 | Furey | 252/34 X |

FOREIGN PATENT DOCUMENTS

93256 1/1960 Netherlands .......................... 252/54.6
859732 1/1961 United Kingdom ................... 252/54.6

*Primary Examiner*—Andrew Metz
*Attorney, Agent, or Firm*—Luther A. R. Hall

[57] ABSTRACT

Compounds of the general formula I

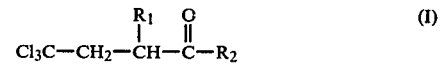

in which $R_1$ is chlorine or —$CH_2$—$CCl_3$, and
$R_2$ is —$N(R_3)R_4$, —$OH.N(R_3)(R_4)R_5$ or —$OR_6$,
$R_3$ is $C_1$–$C_{24}$ alkyl which can be interrupted once or several times by oxygen,
$R_4$ and $R_5$ independently of one another are hydrogen or $C_1$–$C_{24}$ alkyl, with $R_3$ and $R_4$ together having at least 8 C atoms,
$R_6$ is $C_8$–$C_{20}$ alkyl, phenyl or $C_7$–$C_{15}$ alkylphenyl, a group of the formula —(A)$R_7$ or —$CH_2CH_2$—$N(R_{10})$—$CH_2CH_2$—O—C(O)—CH($R_1$)$CH_2CCl_3$, wherein
$R_7$ is a radical of the formula —($R_8$)C($R_9$)—O—C-(O)—CH($R_1$)—$CH_2$—$CCl_3$, wherein
$R_8$ and $R_9$ independently of one another are hydrogen, methyl or ethyl, and $R_1$ has the meaning defined above,
A is a $C_1$–$C_7$ alkylene group which is unsubstituted or substituted by one or two radicals $R_7$ or by one or two methyl or ethyl groups, and which can be interrupted by —O—, and
$R_{10}$ is $C_4$–$C_{20}$ alkyl.

12 Claims, No Drawings

CHLORINATED DERIVATIVES OF BUTYRIC ACID AS USEFUL LUBRICANT ADDITIVES AND LUBRICANTS CONTAINING SAME

LUBRICANT ADDITIVES

The present invention relates to novel chlorinated derivatives of butyric acid, to their use as lubricant additives, to the production thereof, and to the lubricants containing the novel compounds.

Various additives are in general added to mineral and synthetic lubricants in order to improve the performance characteristics of these lubricants. There is in particular a need for additives able to protect the devices to be lubricated from frictional wear. The requirement which wear inhibitors of this kind are expected to meet is that they increase the load-bearing capacity of the lubricant and do not have a corrosive action on the metal parts to be protected. The use of $\alpha,\alpha,\gamma,\gamma$-tetrachlorobutyric acid as an additive for lubricants is known from the German Auslegeschrift No. 1,033,355. This compound has though a corrosive action, which greatly limits its commercial applicability. In the French patent specification No. 1,242,382, there have furthermore been described lower alkyl esters of $\alpha,\alpha,\gamma,\gamma$-tetrachlorobutyric acid, the effectiveness of these however does not meet the high requirements. There have also been suggested ammonium salts of halogenated carboxylic acids, such as for example of $\alpha,\alpha,\gamma$-trichlorobutyric acid, lubricant additives in the U.S. Pat. No. 3,785,977. Such compounds have however the disadvantage that they are susceptible to hydrolysis, and become dissolved by water which has penentrated, the consequence of which is an impairment of their wear-retarding and high-pressure properties.

There has now been found a class of chlorinated butyric acid derivatives which are extremely effective as high-pressure and antiwear additives in lubricants and in cutting oils, and which exhibit, besides negligible volatility, also minimum water-solubility, as a result of which a reduction of active substance due to removal by water scarcely occurs in the lubricating system. The novel substances are rendered particularly valuable by virtue of the combination of the stated properties with the excellent anticorrosive action of these substances.

The novel compounds correspond to the general formula I

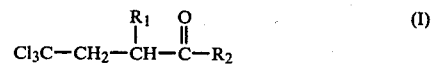
(I)

in which $R_1$ is chlorine or $-CH_2-CCl_3$, and $R_2$ is $-N(R_3)R_4$, $-OH.N(R_3)(R_4)R_5$ or $-OR_6$, wherein $R_3$ is $C_1-C_{24}$ alkyl, which can be interrupted once or several times by oxygen, $R_4$ and $R_5$ independently of one another are hydrogen or $C_1-C_{24}$ alkyl, with $R_3$ and $R_4$ together having at least 8 C atoms, $R_6$ is $C_8-C_{20}$ alkyl, phenyl or $C_7-C_{15}$ alkylphenyl, a group of the formula $-(A)R_7$ or $-CH_2CH_2-N(R_{10})-CH_2CH_2-O-C(O)-CH(R_1)CH_2CCl_3$, wherein $R_7$ is a radical of the formula $-(R_8)C(R_9)-O-C-(O)-CH(R_1)-CH_2-CCl_3$, wherein $R_8$ and $R_9$ independently of one another are hydrogen, methyl or ethyl, and $R_1$ has the meaning defined above, A is a $C_1-C_7$ alkylene group which is unsubstituted or substituted by one or two radicals $R_7$ or by one or two methyl or ethyl groups, and which can be interrupted by $-O-$, and $R_{10}$ is $C_4-C_{20}$ alkyl.

As $C_1-C_{24}$ alkyl and preferably $C_4-C_{18}$ alkyl, $R_3$, $R_4$ and $R_5$ are for example methyl, ethyl, n-propyl, isopropyl, n-butyl, sec-butyl, tert-butyl, n-pentyl, tert-pentyl, isopentyl, neopentyl, n-hexyl, isohexyl, heptyl, octyl, 1,1,3,3-tetramethylbutyl, 2-ethylhexyl, n-octyl, decyl, undecyl, 1,1,3,3,5,5-hexamethylhexyl, n-dodecyl, tridecyl, tetradecyl, pentadecyl, hexadecyl, heptadecyl, octadecyl, nonadecyl, eicosyl, heneicosyl, docosyl, tricosyl or tetracosyl, dodecacosyl-ethyl, isotridecyloxyethyl or isononyloxypropyl. Preferred compounds are those in which at least one of the radicals $R_3$, $R_4$ or $R_5$ is $C_8-C_{18}$ alkyl. Also preferred however are compounds in which $R_4$ or $R_4$ and $R_5$ are hydrogen.

As $C_8-C_{24}$ alkyl, $R_6$ can be for example n-octyl, 1,1,3,3-tetramethylbutyl, 2-ethylhexyl, nonyl, decyl, n-dodecyl, 1,1,3,3,5,5-hexamethylhexyl, tridecyl, tetradecyl, pentadecyl, hexadecyl, heptadecyl, octadecyl, nonadecyl, eicosyl, heneicosyl, docosyl, tricosyl or tetracosyl. As an alkyl group, $R_6$ is preferably an alkyl group having 8-18 C atoms.

As alkylphenyl having 7-15 C atoms, $R_6$ is for example 2,4-di-tert-butylphenyl, 2,6-di-tert-butyl-4-methylphenyl or p-nonylphenyl.

In the case of various long-chain alkyl groups given above as examples for $R_4$, $R_5$ and $R_6$, no pure isomers are mentioned. The reason for this is on the one hand that isomeric mixtures are just as suitable as pure isomers as lubricant additives, and on the other hand that the alcohols and amines used for producing the compounds of the formula I are frequently offered commercially as isomeric mixtures or even as mixtures of compounds which contain alkyl groups of different length. As an example there may be mentioned Primen 81-R (Röhm and Haas, USA), which is a mixture of primary $C_{12}-C_{15}$ alkylamines of differing isomerism.

If $R_6$ is a group of the formula $-(A)R_7$, then A as a $C_1-C_8$ alkylene group, which can be interrupted by $-O-$, is for example methylene, dimethylene, trimethylene, tetramethylene, hexamethylene, heptamethylene or 3,6-dioxa-heptamethylene, preferably methylene, dimethylene or 3,6-dioxa-heptamethylene. If A is an alkylene group substituted by one or two methyl or ethyl groups, it is for example 1,1-dimethyldimethylene, 1-methyl-1-ethyldimethylene or dimethylmethylene. Alkylene groups A substituted by radicals $R_7$ are for example $-CH(R_7)-$, $-CH_2CH_2CH(R_7)-CH_2-$ or $-CH_2-C(R_7)_2-$.

$R_8$ and $R_9$ are ethyl, preferably methyl and particularly preferably hydrogen. Preferred compounds are those in which $R_8$ and $R_9$ have the same meaning.

As $C_4-C_{20}$ alkyl, $R_{10}$ can be for example n-butyl, sec-butyl, tert-butyl, n-pentyl, isopentyl, neopentyl, isohexyl, n-hexyl, n-octyl, 2-ethylhexyl, decyl, dodecyl, tetradecyl, octadecyl or eicosyl.

Preferred compounds of the formula I are those wherein $R_1$ is chlorine or $-CH_2-CCl_3$, $R_2$ is $-N(R_3)R_4$, $-OH.N(R_3)(R_4)R_5$ or $-OR_6$, $R_3$ is $C_4-C_{18}$ alkyl, $R_4$ and $R_5$ independently of one another are hydrogen or $C_4$-$C_{18}$ alkyl, with $R_3$ and $R_4$ together having at least 8 C atoms, $R_6$ is $C_8$-$C_{18}$ alkyl or $C_7$-$C_{15}$ alkylphenyl, or a group of the formula —(A)$R_7$ wherein $R_7$ is a radical of the formula —($R_8$)C($R_9$)—O—C-(O)—CH($R_1$)—CH$_2$—CCl$_3$, wherein $R_8$ and $R_9$ independently of one another are hydrogen, methyl or ethyl, and $R_1$ has the meaning defined above, and A is a $C_1$-$C_5$ alkylene group which is unsubstituted or substituted by one or two radicals $R_7$ or by one or two methyl or ethyl groups, or it is a 3,6-dioxaheptamethylene group.

Particularly preferred compounds of the formula I are those in which $R_1$ is chlorine or —CH$_2$—CCl$_3$, $R_2$ is —N($R_3$)$R_4$, —OH.N($R_3$)($R_4$)$R_5$ or —O$R_6$, $R_3$ is $C_4$-$C_{18}$ alkyl, $R_4$ and $R_5$ independently of one another are hydrogen or $C_4$-$C_{18}$ alkyl, with $R_3$ and $R_4$ together having at least 8 C atoms, $R_6$ is $C_8$-$C_{18}$ alkyl, $C_7$-$C_{15}$ alkylphenyl, or a group of the formula —(A)$R_7$, wherein $R_7$ is a radical of the formula —CH$_2$—O—C-(O)—CH($R_1$)—CH$_2$—CCl$_3$, wherein $R_1$ has the meaning defined above, and A is $C_1$-$C_5$ alkylene, 3,6-dioxaheptamethylene, or one of the groups of the formula —CH($R_7$), —CH$_2$CH$_2$CH($R_7$)—CH$_2$— or —CH$_2$—C($R_7$)$_2$, wherein $R_7$ has the meaning defined above.

Examples of compounds of the formula I are:

(1) 2,4,4,4-tetrachlorobutyric acid-N-octadecylamide,
(2) bis-(2',2',2'-trichloroethyl)-acetic acid-N-dodecylamide,
(3) the
 (a) octadecylammonium salt of (i)/(ii),
 (b) dioctylammonium salt of (i)/(ii),
 (c) di-n-butylammonium salt of (i)/(ii),
 (d) tri-n-butylammonium salt of (i)/(ii),
 (e) dodecylammonium salt of (i)/(ii),
 (f) 1,1,3,3-tetramethylbutylammonium salt of (i)/(ii),
 (g) mixture of the eicosyl-bis-docosylammonium salts of (i)/(ii),
  (i) 2,4,4,4-tetrachlorobutyric acid or
  (ii) bis-(2',2',2'-trichloroethyl)-acetic acid,
(4) 2,4,4,4-tetrachlorobutyric acid octadecyl ester,
(5) bis-(2',2',2'-trichloroethyl)-acetic acid dodecyl ester,
(6) bis-(2',2',2'-trichloroethyl)-acetic acid-2-ethylhexyl ester,
(7) X—O—CH$_2$—CH$_2$—O—X, Y—O—CH$_2$—CH$_2$—O—Y,
(8) (X—O—CH$_2$)$_2$—CH—O—X), (Y—O—CH$_2$)$_2$—CH—O—Y,
(9) (X—O—CH$_2$)$_4$—C, (Y—O—CH$_2$)$_4$—C,
(10) (X—O—CH$_2$—CH$_2$)$_2$—O, (Y—O—CH$_2$—CH$_2$)$_2$—O,
(11) X—O—CH$_2$—C(CH$_3$)$_2$—CH$_2$O—X, Y—O—CH$_2$—C(CH$_3$)$_2$—CH$_2$—O—Y,
(12) X—O—CH$_2$—CH$_2$—O—CH$_2$—CH$_2$—O—CH$_2$—CH$_2$—O—X, Y—O—CH$_2$—CH$_2$—O—CH$_2$CH$_2$—O—CH$_2$—CH$_2$—O—Y,
(13) CH$_3$—C(CH$_2$—O—X)$_3$, CH$_3$—C(CH$_2$—O—Y)$_3$,
(14) CH$_3$CH$_2$—C(CH$_2$—O—X)$_3$, CH$_3$CH$_2$—C(CH$_2$O—Y)$_3$,
(15) H$_{25}$C$_{12}$N—(CH$_2$—CH$_2$—O—X)$_2$, H$_{25}$C$_{12}$N—(CH$_2$—CH$_2$—O—Y)$_2$,
(16) H$_{37}$C$_{18}$N—(CH$_2$—CH$_2$—O—X)$_2$, H$_{37}$C$_{18}$N—(CH$_2$—CH$_2$—O—Y)$_2$,
(17) mixture of 2,4,4,4-tetrachlorobutyric acid-$C_{20}$-$C_{22}$-alkylamides.

The meanings of X and Y in the compounds 7 to 16 are:

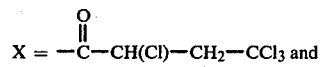

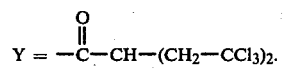

The compounds of the formula I can be produced by methods known per se, in particular by subjecting a compound of the formula II

in which $R_1$ is as defined above, or a reactive derivative thereof, to the customary esterification, amidation or salt-forming reactions. Suitable reactants for esterification reactions are alcohols of the formula HO—$R_6$, suitable reactants for amidation reactions are amines of the formula HN($R_3$)$R_4$, and suitable reactants for salt-forming reactions are amines of the formula $R_3$N($R_4$)$R_5$.

A further possibility of obtaining products of the formula I wherein $R_1$ is Cl and $R_2$ is —N($R_3$)$R_4$ or —O$R_6$, and the remaining symbols have the meanings defined above, is to react, in a manner known per se, an acrylic acid derivative of the formula CH$_2$=CH—C-(O)$R_2$, in which $R_2$ is —N($R_3$)$R_4$ or —O$R_6$ and $R_3$, $R_4$ and $R_6$ are as defined above, in the presence of a catalyst, optionally in a solvent, with carbon tetrachloride. It is known that suitable catalysts for halogenation are for example FeCl$_2$, FeCl$_3$ and especially CuCl.

It is obvious that it is possible also to obtain the desired products by customary transesterification or transamidation or salt-converting reactions.

2,4,4,4-Tetrachlorobutyric acid is a known compound and can be produced for example according to the Israel patent specification No. 18771=C.A., 13089e (1965); whilst bis-(2',2',2'-trichloroethyl)-acetic acid can be produced by a process analogous to the process described for the acid chloride in Example 2 from dichloroacetic acid and 1,1-dichloroethylene. Both the free acid and the chloride thereof are novel compounds, and are suitable for example as intermediates for producing compounds of the formula I wherein $R_1$ is —CH$_2$—CCl$_3$, and $R_2$ has the meaning defined above.

The alcohols and amines used for the reaction have been known compounds for a long time, and in many cases are commercial products.

Even in very small amounts, the compounds of the formula I act as high-pressure additives in lubricants. Thus, mineral and synthetic lubricating oils, and also mixtures thereof, which contain 0.001 to 5 percent by weight, and preferably 0.02 to 3 percent by weight, relative to the lubricant, of a compound of the formula I display excellent high-pressure lubricating properties which are clearly shown in greatly reduced wear phenomena on the parts between which rubbing occurs and which are hence to be lubricated. The lubricants which can be used are commonly known to those skilled in the art, and are described for example in "Schmiermittel Taschenbuch" ("Lubricants Handbook") (Hüthig Verlag, Heidelberg, 1974).

The lubricating oil formulation can additionally contain other additives which are added in order to improve certain basic oil properties, such as antioxidants, metal passivators, rust inhibitors, agents for improving the viscosity index, pour-point depressors, dispersants/detergents and other additives which protect against wear.

Examples of *antioxidants* are:

(a) alkylated and non-alkylated aromatic amines and mixtures thereof, for example: dioctyldiphenylamine, mono-t-octylphenyl-α- and -β-naphthylamines phenothiazine, dioctylphenothiazine, phenyl-α-naphthylamine and N,N'-di-sec-butyl-p-phenylenediamine;

(b) sterically hindered phenols, for example 2,6-di-tert-butyl-p-cresol, 4,4'-bis-(2,6-diisopropylphenol), 2,4,6-triisopropylphenol, 2,2'-thio-bis-(4-methyl-6-tert-butylphenol) and 4,4'-methylene-bis-(2,6-di-tert-butyl-phenol);

(c) alkyl phosphites, aryl phosphites or alkaryl phosphites, for example: trinonyl phosphite, triphenyl phosphite and diphenyldecyl phosphite;

(d) esters of thiodipropionic acid or thiodiacetic acid, for example: dilauryl thiodipropionate or dioctyl thiodiacetate;

(e) salts of carbamic and dithiophosphoric acids, for example: antimony diamyldithiocarbamate and zinc diamyldithiophosphate; and (f) combinations of two or more antioxidants from the above, for example: an alkylated amine and a sterically hindered phenol.

Examples of *metal passivators* are:

(a) for copper, for example, benztriazole, tetrahydrobenztriazole, 2-mercaptobenzthiazole, 2,5-dimercaptothiadiazole, salicylidene-propylenediamine and salts of salicylaminoguanidine;

(b) for lead, for example, sebacic acid derivatives, quinizarine and propyl gallate; and (c) a combination of two or more of the above additives.

Examples of *rust inhibitors* are:

(a) organic acids and their esters, metal salts and anhydrides, for example: N-oleoyl-sarcosine, sorbitane monooleate, lead naphthenate and dodecenylsuccinic anhydride;

(b) nitrogen-containing compounds, for example:

I. primary, secondary or tertiary aliphatic or cycloaliphatic amines and amine salts or organic and inorganic acids, for example oil-soluble alkyl-ammonium carboxylates, and II. heterocyclic compounds, for example: substituted imidazolines and oxazolines;

(c) phosphorus-containing compounds, for example: amine salts of phosphoric acid partial esters;

(d) sulfur-containing compounds, for example: barium dinonylnaphthalene-sulfonates and calcium petroleum sulfonates; and (e) combinations of two or more of the above additives.

Examples of *agents which improve the viscosity index* are, for example: polymethacrylates, vinylpyrrolidone/methacrylate copolymers, polybutenes, olefine copolymers and styrene/acrylate copolymers.

Examples of *pour-point depressors* are, for example: polymethacrylates and alkylated naphthalene derivatives.

Examples of *dispersants/detergents* are, for example: polybutenylsuccinic acid imides, polybutenylphosphonic acid derivatives and hyperbasic sulfonates and phenolates of magnesium, calcium and barium.

Examples of other *additives which provide protection against wear* are, for example: compounds which contain sulfur and/or phosphorus and/or halogen, such as vegetable oils treated with sulfur, zinc dialkyldithiophosphates, tritolyl phosphate, chlorinated paraffins, alkyl disulfides and aryl disulfides.

The Examples which follow illustrate the invention.

EXAMPLE 1

226 g (1 mol) of 2,4,4,4-tetrachlorobutyric acid, 600 g of thionyl chloride and 1 ml of N,N-dimethylformamide are heated for 2 hours at 50° C. and for 2 hours at 75° C. After the unreacted thionyl chloride has been evaporated off, the residue is distilled. The yield is 227.6 g (93% of theory) of 2,4,4,4-tetrachlorobutyric acid chloride; b.p. 90°–91° C./15 mm Hg.

EXAMPLE 2

147.4 g (1 mol) of dichloroacetic acid chloride, 291.8 g (3 mols) of 1,1-dichloroethylene, 300 ml of acetonitrile and 3.0 g of copper(I)chloride are heated at 160° C. in an autoclave for 6 hours. The reaction solution is thereupon filtered, concentrated by evaporation and distilled. The fraction distilling over at b.p. 160°–165° C./13 Torr is collected. The yield is 182.1 g (53% of theory) of bis-(2',2',2'-trichloroethyl)-acetic acid chloride in the form of a slightly yellow liquid.

EXAMPLE 3

191.0 g of Primen 81-R (mixture of primary $C_{12}$–$C_{15}$ tert-alkylamines, from Röhm and Haas, U.S.A.) is dissolved in 500 ml of glacial acetic acid, 500 ml of water and 2 200 g of crystallised sodium acetate. There are then added dropwise at 0°–5° C. 244 g of 2,4,4,4-tetrachlorobutyric acid chloride. The temperature of the reaction mixture is allowed to rise within 2 hours to room temperature; 2000 ml of water are added and the mixture is extracted with 2000 ml of toluene. The toluene phase is washed with a 10% aqueous solution of sodium hydrogen carbonate and subsequently with water. The toluene is distilled off in vacuo to leave 352.0 g (83% of theory) of a light-yellow viscous oil, which is a mixture of $C_{12}$–$C_{15}$ alkylamides of 2,4,4,4-tetrachlorobutyric acid (Additive No. 1).

EXAMPLE 4

If in Example 3 the 2,4,4,4-tetrachlorobutyric acid chloride is replaced by 341.2 g of bis-(2',2',2'-trichloroethyl)-acetic acid chloride, the procedure otherwise being the same, there is obtained 390.0 g of a light-yellow viscous oil, which is a mixture of $C_{12}$–$C_{15}$ alkylamides of bis-(2',2',2'-trichloroethyl)-acetic acid (Additive No. 2).

EXAMPLE 5

244.4 g (1.0 mol) of 2,4,4,4-tetrachlorobutyric acid chloride (produced according to Example 1) is slowly added to 30.4 g (0.33 mol) of anhydrous glycerol. After the exothermic reaction has subsided, the reaction mixture is heated at 120°–125° C. for 5 hours. It is subsequently distilled under high vacuum, and the fraction boiling at b.p. 155°–157° C./0.1 Torr is collected. There is obtained 182.6 g of an almost colourless, viscous liquid of the formula

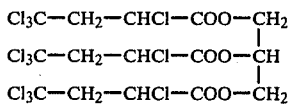

(Additive No. 3).

EXAMPLE 6

244.4 g of 2,4,4,4-tetrachlorobutyric acid chloride (1.0 mol) is slowly added to 270.5 g of 1-octadecanol (1.0 mol) as a melt at 60° C., and the mixture is heated for 5 hours at 120°–125° C. There is obtained 470.5 g of a very viscous light-yellow liquid, which is not distillable under high vacuum at 0.1 Torr and 220° C. The product is 2,4,4,4-tetrachlorobutyric acid octadecyl ester (Additive No. 4).

EXAMPLE 7

If in Example 5 the glycerol is replaced by 220.3 g of p-nonylphenyl (Montedison), the procedure otherwise being the same, there is obtained 460.3 g of 2,4,4,4-tetrachlorobutyric acid-p-nonylphenyl ester in the form of a brown oil, which can be distilled under high vacuum at 0.1 Torr between 160° and 170° C. (Additive No. 5).

EXAMPLE 8

If the glycerol in Example 5 is replaced by 75.1 g (0.5 mol) of triethylene glycol, the procedure otherwise being the same, there is obtained, after heating under high vacuum at 0.1 Torr at 180° C., 230.7 g of a light-brown, very viscous oil of the formula

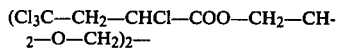

(Additive 6).

EXAMPLE 9

If the glycerol in Example 5 is replaced by 59.1 g (0.5 mol) of 1,6-hexanediol, the procedure otherwise remaining the same, there is obtained, after distilling off small amounts of starting material at 180° C. in vacuo (0.1 Torr), 210.8 g of a slightly yellow, very viscous oil of the formula

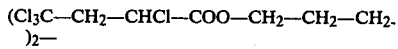

(Additive No. 7).

EXAMPLE 10

341.2 g of bis-(2',2',2'-trichloroethyl)-acetic acid chloride (1.0 mol) (from Example 2) is slowly added to 150.0 g of 2-ethylhexanol (1.15 mol), and the mixture is then heated at 120° C. for 6 hours. The unreacted 2-ethylhexanol is subsequently distilled off in vacuo at 12 Torr and 100°–120° C. to leave 434.1 g of a light-yellow viscous oil, which is not distillable under high vacuum (0.1 Torr). The product is bis-(2',2',2'-trichloroethyl)-acetic acid-(2-ethylhexyl)-ester (Additive No. 8).

EXAMPLE 11

If the bis-(2',2',2'-trichloroethyl)-acetic acid chloride in Example 10 is replaced by 244.4 g (1 mol) of 2,4,4,4-tetrachlorobutyric acid chloride, the procedure otherwise being the same, there is obtained 330.2 g of 2,4,4,4-tetrachlorobutyric acid-(2-ethylhexyl)-ester in the form of a viscous almost colourless oil, which boils at 114°–116° C./2 Torr and corresponds to the formula

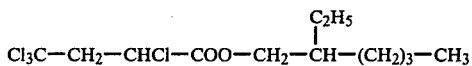

(Additive No. 9).

EXAMPLE 12

6.6 g (0.03 mol) of 2,4,4,4-tetrachlorobutyric acid is dissolved in 50 ml of toluene, and 5.8 g (0.03 mol) of Primene 81-R (mixture of primary $C_{12}$–$C_{15}$ t-alkylamines, Rohm and Haas, U.S.A.) is added with stirring. The solvent is completely distilled off under reduced pressure to leave a yellowish transparent oil readily soluble in hexane or mineral oil, the oil obtained being a mixture of dodecyl- to pentadecylammonium salts of 2,4,4,4-tetrachlorobutyric acid (Additive No. 10).

If the Primene 81-R in this Example is replaced by an equivalent amount of diisooctylamine or diisotridecylamine, the procedure otherwise being unchanged, there are obtained the corresponding ammonium salts in the form of yellowish transparent oils, namely the diisooctylammonium salt of 2,4,4,4-tetrachlorobutyric acid (Additive No. 11) and the diisotridecylammonium salt of 2,4,4,4-tetrachlorobutyric acid (Additive No. 12).

EXAMPLE 13

The following values were determined using the Shell four-ball apparatus (Tentative method IP 239/69, extreme pressure and wear lubricant test for oils and greases, four-ball machine).

(1) I.S.L.=Initial Seizure Load: that is the load under which the oil film breaks down within a duration of load application of 10 seconds.

(2) W.L.=Weld Load: that is the load under which the 4 balls weld together within 10 seconds.

(3) W.S.D.=Wear Scar Diameter in mm: that is the mean wear diameter when a load of 40 kg is applied for 1 hour.

Vitrea 41 (Shell tradename) was used as the base oil.

TABLE 1

| Additive No. | Concentration In % by weight | ISL (kg) | WL (kg) | WSD (mm) |
|---|---|---|---|---|
| none | — | 60 | 160 | 1.1 |
| 1 | 1% | 80 | 400 | 0.8 |
| 3 | 1% | 130 | 270 | 0.7 |
| 4 | 1% | — | >200 | 0.6 |
| 5 | 1% | 100 | 230 | 0.9 |
| 6 | 1% | — | >200 | 0.5 |
| 7 | 1% | — | >200 | 0.5 |
| 8 | 1% | 110 | 250 | 0.8 |
| 9 | 1% | 110 | 250 | 0.8 |
| 10 | 1% | 160 | 500 | 0.8 |
| 11 | 1% | — | >200 | 1.1 |
| 12 | 1% | — | >200 | 0.5 |

EXAMPLE 14

The exceptional load-bearing properties of the lubricant additives according to the invention are shown in the test in the FZG gear wheel distortion test rig.

For this purpose, mixtures of the additives according to the invention in a non-doped mineral lubricating oil (viscosity: 20 cSt/50° C) were prepared and tested using the FZG machine according to DIN 51354 (standard test A/8.3/90). For comparison, the non-doped mineral lubricating oil without an additive was also tested on the FZG machine.

The results of these tests are summarised in Table 2 given below.

TABLE 2

| Test No. | Additive No. | Concentration % by weight | Load stage at which damage occurs |
|---|---|---|---|
| 1 | none | — | 6–7 |
| 2 | chlorinated paraffin 50* | 0.5 | 7 |
| 3 | 1 | 0.5 | 11 |
| 4 | 3 | 0.5 | 11 |
| 5 | 12 | 0.5 | 12 |

*ex Hoechst ®

From these results can be seen the outstanding load-bearing properties of the compounds according to the invention.

What is claimed is:

1. A compound of the general formula I

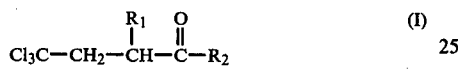

$$Cl_3C-CH_2-CH(R_1)-C(=O)-R_2 \quad (I)$$

in which
$R_1$ is chlorine or $-CH_2-CCl_3$, and
$R_2$ is $-N(R_3)R_4$, $-OH.N(R_3)(R_4)R_5$ or $-OR_6$ wherein
$R_3$ is $C_1-C_{24}$ alkyl, which can be interrupted once or several times by oxygen,
$R_4$ and $R_5$ independently of one another are hydrogen or $C_1-C_{24}$ alkyl, with $R_3$ and $R_4$ together having at least 8 C atoms,
$R_6$ is $C_8-C_{20}$ alkyl, phenyl or $C_7-C_{15}$ alkylphenyl, a group of the formula $-(A)R_7$ or $-CH_2CH_2-N(R_{10})-CH_2CH_2-O-C(O)-CH(R_1)CH_2CCl_3$, wherein
$R_7$ is a radical of the formula $-(R_8)C(R_9)-O-C(O)-CH(R_1)-CH_2-CCl_3$, wherein
$R_8$ and $R_9$ independently of one another are hydrogen, methyl or ethyl, and $R_1$ has the meaning defined above,
A is a $C_1-C_7$ alkylene group which is unsubstituted or substituted by one or two radicals $R_7$ or by one or two methyl or ethyl groups, and which can be interrupted by $-O-$, and
$R_{10}$ is $C_4-C_{20}$ alkyl.

2. A compound according to claim 1 of the formula I in which
$R_1$ is chlorine or $-CH_2-CCl_3$, and
$R_2$ is $-N(R_3)R_4$, $-OH.N(R_3)(R_4)R_5$ or $-OR_6$,
$R_3$ is $C_4-C_{18}$ alkyl,
$R_4$ and $R_5$ independently of one another are hydrogen or $C_4-C_{18}$ alkyl, with $R_3$ and $R_4$ together having at least 8 C atoms,
$R_6$ is $C_8-C_{18}$ alkyl or $C_7-C_{15}$ alkylphenyl, or a group of the formula $-(A)R_7$ wherein
$R_7$ is a radical of the formula $-(R_8)C(R_9)-O-C(O)-CH(R_1)-CH_2-CCl_3$, wherein
$R_8$ and $R_9$ independently of one another are hydrogen, methyl or ethyl, and $R_1$ has the meaning defined above, and
A is a $C_1-C_5$ alkylene group which is unsubstituted or substituted by one or two radicals $R_7$ or by one or two methyl or ethyl groups, or it is a 3,6-dioxaheptamethylene group.

3. A compound according to claim 1 of the formula I, in which
$R_1$ is chlorine or $-CH_2-CCl_3$,
$R_2$ is $-N(R_3)R_4$, $-OH.N(R_3)(R_4)R_5$ or $-OR_6$,
$R_3$ is $C_4-C_{18}$ alkyl,
$R_4$ and $R_5$ independently of one another are hydrogen or $C_4-C_{18}$ alkyl, with $R_3$ and $R_4$ together having at least 8 C atoms,
$R_6$ is $C_8-C_{18}$ alkyl, $C_7-C_{15}$ alkylphenyl or a group of the formula $-(A)R_7$, wherein
$R_7$ is a radical of the formula $-CH_2-O-C(O)-CH(R_1)-CH_2-CCl_3$, wherein $R_1$ has the meaning defined above, and
A is $C_1-C_5$ alkylene, 3,6-dioxaheptamethylene, or one of the groups of the formulae $-CH(R_7)-$, $-CH_2CH_2CH(R_7)-CH_2$ or $-CH_2-C(R_7)_2-$, wherein $R_7$ has the meaning defined above.

4. A compound according to claim 1 of the formula I wherein $R_1$ is Cl.

5. A compound according to claim 1 of the formula I, wherein $R_1$ is $-CH_2-CCl_3$.

6. A compound according to claim 1 of the formula I wherein $R_2$ is $-N(R_3)R_4$.

7. A compound according to claim 1 of the formula I wherein $R_2$ is $-OH.N(R_3)(R_4)R_5$.

8. A compound according to claim 1 of the formula I wherein $R_2$ is $-OR_6$.

9. Di-(2,2,2-trichloroethyl)acetic acid $(Cl_3CCH_2)_2CHCOOH$.

10. Di-(2,2,2-trichloroethyl)acetylchloride, $(CL_3CCH_2)_2CHCOCl$.

11. A composition comprising a major proportion of an oil of lubricating viscosity and 0.001 to 5 percent by weight, relative to the composition, of a compound of the formula I according to claim 1.

12. A method of providing an oil of lubricating viscosity with high-pressure, antiwear and anticorrosive properties which comprises adding thereto 0.001 to 5 percent by weight, relative to the oil, of a compound of the formula I according to claim 1.

* * * * *

Disclaimer 4,263,157.—*Eginhard Steiner*, Fullinsdorf and *Andreas Schmidt*, Reinach, Switzerland, CHLORINATED DERIVATIVES OF BUTYRIC ACID AS USEFUL LUBRICANT ADDITIVES AND LUBRICANTS CONTAINING SAME. Patent dated Apr. 21, 1981. Disclaimer filed July 9, 1981, by the assignee, *Ciba-Geigy Corp.*

Hereby enters this disclaimer to claims 1, 2, 3, 4 and 8 of said patent.

[*Official Gazette August 22, 1981.*]

UNITED STATES PATENT AND TRADEMARK OFFICE
CERTIFICATE OF CORRECTION

PATENT NO. : 4,263,157
DATED : APRIL 21, 1981
INVENTOR(S) : EGINHARD STEINER AND ANDREAS SCHMIDT

It is certified that error appears in the above—identified patent and that said Letters Patent is hereby corrected as shown below:

Claim 10, Column 10, lines 44 and 45 read:

"Di-(2,2,2-trichloroethyl)acetylchloride, $(CL_3CCH_2)_2CHCOCl$."

Should read:

"Di-(2,2,2-trichloroethyl)acetyl chloride, $(Cl_3CCH_2)_2CHCOCl$."

Signed and Sealed this

Second Day of March 1982

[SEAL]

Attest:

Attesting Officer

GERALD J. MOSSINGHOFF
Commissioner of Patents and Trademarks